United States Patent
Suzuki et al.

(10) Patent No.: US 11,478,123 B2
(45) Date of Patent: Oct. 25, 2022

(54) CONTROL APPARATUS AND SELF-PROPELLED TYPE ENDOSCOPE SYSTEM

(71) Applicant: OLYMPUS CORPORATION, Tokyo (JP)

(72) Inventors: Takashi Suzuki, Hino (JP); Fumiyuki Onoda, Tama (JP); Takashi Yamashita, Hachioji (JP); Yasuaki Natori, Akishima (JP); Yoshitaka Umemoto, Hachioji (JP); Toshihiro Kumagai, Hino (JP); Takuro Onda, Sagamihara (JP)

(73) Assignee: OLYMPUS CORPORATION, Tokyo (JP)

( * ) Notice: Subject to any disclaimer, the term of this patent is extended or adjusted under 35 U.S.C. 154(b) by 162 days.

(21) Appl. No.: 16/737,368

(22) Filed: Jan. 8, 2020

(65) Prior Publication Data
US 2020/0138266 A1     May 7, 2020

Related U.S. Application Data (63) Continuation of application No. PCT/JP2018/018098, filed on May 10, 2018.

(30) Foreign Application Priority Data

Jul. 12, 2017 (JP) .............................. JP2017-136236

(51) Int. Cl.
*A61B 1/00* (2006.01)
*G02B 23/24* (2006.01)

(52) U.S. Cl.
CPC ........ *A61B 1/00006* (2013.01); *A61B 1/0016* (2013.01); *A61B 1/00133* (2013.01); *G02B 23/2476* (2013.01)

(58) Field of Classification Search
CPC ............ A61B 1/00006; A61B 1/00071; A61B 1/00112; A61B 1/00131; A61B 1/00133;
(Continued)

(56) References Cited

U.S. PATENT DOCUMENTS

2008/0009675 A1* 1/2008 Kura ................... A61B 1/00156
600/137
2008/0086029 A1* 4/2008 Uchiyama ................ A61B 1/01
600/114
(Continued)

FOREIGN PATENT DOCUMENTS

JP      2007-185390 A     7/2007
JP      2007-306993 A    11/2007
(Continued)

OTHER PUBLICATIONS

Japanese Office Action dated Jul. 7, 2020 in Japanese Patent Application No. 2019-528948.
(Continued)

*Primary Examiner* — Ryan N Henderson
*Assistant Examiner* — Pamela F Wu
(74) *Attorney, Agent, or Firm* — Scully, Scott, Murphy & Presser, P.C.

(57) ABSTRACT

A control apparatus controls an operation of a self-propelled mechanism of an endoscope. The control apparatus includes a drive circuit that outputs a motor current, a motor current detection circuit that acquires a value relating to magnitude of the motor current as a detection value, a storage circuit that stores a limit value relating to the detection value, and a control circuit that performs an operation as a first controller that controls the drive circuit so as to stop the motor when it is determined that the detection value exceeds a value relating to the limit value, and performs an operation as a second controller that controls the drive circuit so as to stop the motor when it is determined that the detection value exceeds the value relating to the limit value.

16 Claims, 9 Drawing Sheets

(58) Field of Classification Search
CPC ............ A61B 1/00135; A61B 1/00137; A61B 1/00147; A61B 1/00154; A61B 1/00156; A61B 1/0016; A61B 1/01; A61B 1/00062; G02B 23/2476
USPC ......................................... 600/114, 118, 127
See application file for complete search history.

(56) References Cited

U.S. PATENT DOCUMENTS

| | | | | |
|---|---|---|---|---|
| 2008/0262305 | A1* | 10/2008 | Omoto | A61B 1/00006 600/118 |
| 2009/0156897 | A1* | 6/2009 | Omot | A61B 1/0016 600/118 |
| 2013/0158353 | A1 | 6/2013 | Nakamura et al. | |

FOREIGN PATENT DOCUMENTS

| | | |
|---|---|---|
| JP | 2008-093029 A | 4/2008 |
| JP | 2014-004268 A | 1/2014 |
| WO | WO 2016/159127 A1 | 10/2016 |

OTHER PUBLICATIONS

English translation of International Preliminary Report on Patentability dated Jan. 23, 2020, together with the Written Opinion received in related International Application No. PCT/JP2018/018098.
International Search Report dated Jun. 26, 2018 issued in PCT/JP2018/018098.

* cited by examiner

CONTROL APPARATUS AND SELF-PROPELLED TYPE ENDOSCOPE SYSTEM

CROSS-REFERENCE TO RELATED APPLICATIONS

This application is a Continuation Application of PCT Application No. PCT/JP2018/018098, filed May 10, 2018 and based upon and claiming the benefit of priority from the prior Japanese Patent Application No. 2017-136236, filed Jul. 12, 2017, the entire contents of both of which are incorporated herein by reference.

FIELD

The embodiment relates to a control apparatus which controls an operation of a self-propelled mechanism of an endoscope, and a self-propelled type endoscope system.

BACKGROUND

Generally, an insertion section of an endoscope or the like is inserted into a lumen. Among the endoscopes inserted into a lumen, an endoscope apparatus referred to as a self-propelled type or the like is known.

For example, an endoscope apparatus described in International Publication No. 2016/159127 is a rotary self-propelled type endoscope apparatus. Such a rotary self-propelled type endoscope apparatus is provided, for example, with a rotational tubular body which is called a power spiral tube, etc. in which a spiral-shaped fin is formed on an outer peripheral surface of the insertion section. When the rotational tubular body is rotated, the fin formed in the rotational tubular body is brought into contact with an inner paries of a lumen, and generates propulsive force. The insertion section self-propels in an insertion direction or in a removal direction by the propulsive force. International Publication No. 2016/159127 discloses that a load acting on the rotational tubular body is detected and a rotation of the rotational tubular body is temporarily stopped when the load becomes larger than a predetermined value.

SUMMARY

According to an aspect, a control apparatus controls an operation of a self-propelled mechanism of an endoscope including the self-propelled mechanism configured to move an insertion section forward or backward with a motor as a power source. The control apparatus comprises a drive circuit, a motor current detection circuit, a storage circuit, and a control circuit. The drive circuit outputs a motor current for driving the motor. The motor current detection circuit acquires a value relating to magnitude of the motor current as a detection value. The storage circuit stores a limit value relating to the detection value. The control circuit performs an operation as a first controller that compares the detection value and the limit value and controls the drive circuit so as to stop the motor when it is determined that the detection value exceeds a value relating to the limit value, and performs an operation as a second controller that compares the detection value and the limit value and controls the drive circuit so as to stop the motor when it is determined that the detection value exceeds the value relating to the limit value.

Advantages of the embodiments will be set forth in the description which follows, and in part will be obvious from the description, or may be learned. The advantages may be realized and obtained by means of the instrumentalities and combinations particularly pointed out hereinafter.

BRIEF DESCRIPTION OF THE DRAWINGS

The accompanying drawings, which are incorporated in and constitute a part of the specification, illustrate embodiments, and together with the general description given above and the detailed description of the embodiments given below, serve to explain the principles.

DETAILED DESCRIPTION

An embodiment will be described with reference to the drawings. The embodiment relates to an endoscope system comprising a self-propelled mechanism which generates propulsive force that moves an insertion section of an endoscope forward or backward.

[Configuration of Endoscope System]

Figure 1:
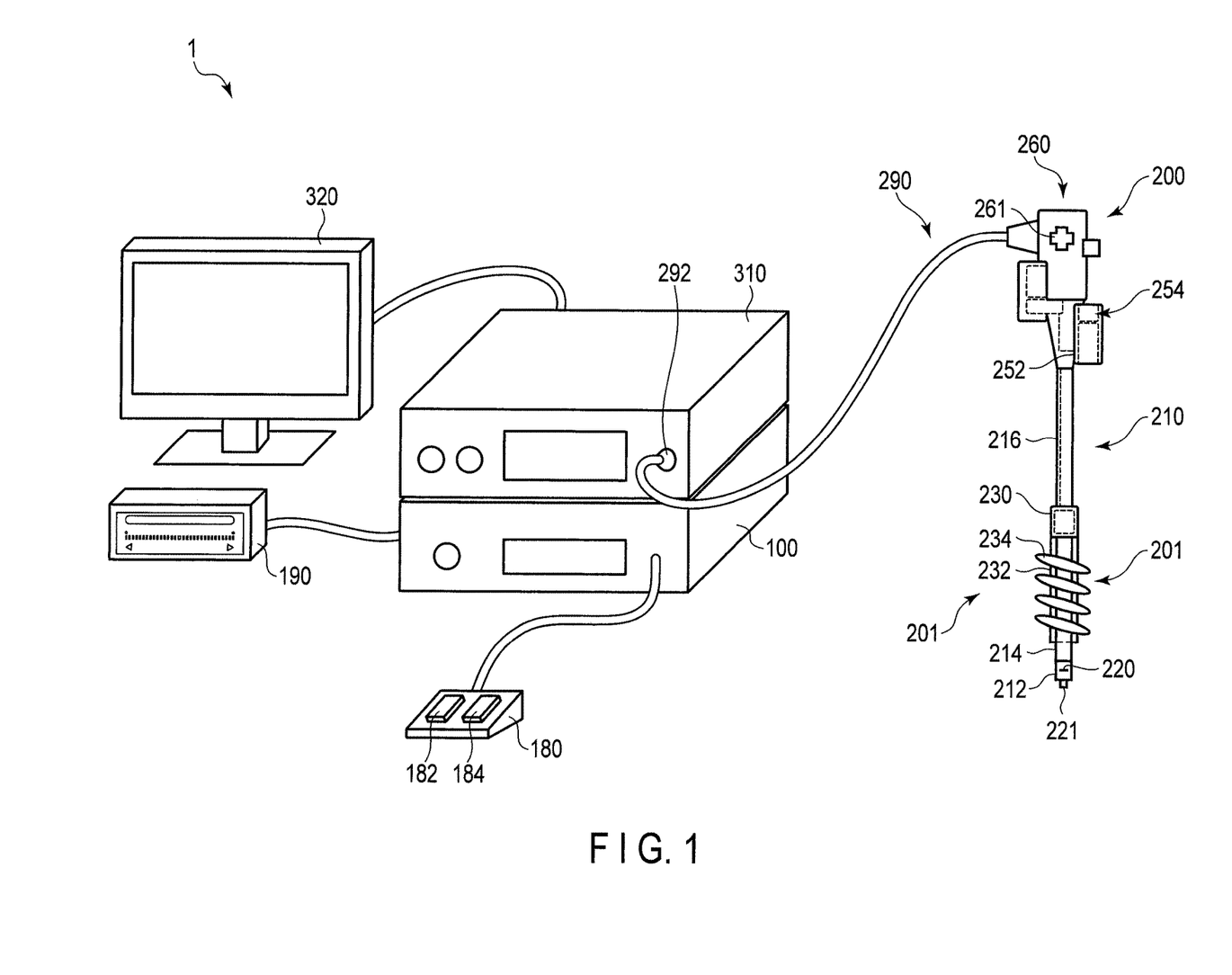
FIG. 1 is a schematic view illustrating an endoscope system configuration example according to an embodiment.

FIG. 1 is a schematic view illustrating a configuration of an endoscope system 1 as an example of an insertion apparatus according to an embodiment. As illustrated in FIG. 1, the endoscope system 1 comprises an endoscope 200, a light source and image processing apparatus 310, a display 320, a control apparatus 100, a foot switch (FSW) 180, and a torque indicator 190.

The endoscope 200 is a rotary self-propelled type endoscope. The endoscope 200 includes an insertion section 210. The insertion section 210 is an elongated shape, and is configured to be inserted into a living body. The endoscope 200 also includes a control unit 260, by which various operations for the endoscope 200 are performed. The control unit 260 is held by a user. Here, a side of a distal end of the insertion section 210 is referred to as a distal end side. In addition, the side of the insertion section 210 where the control unit 260 is provided is referred to as a proximal end side. A direction from the distal end side to the proximal end side of the insertion section 210 is referred to as a longitudinal direction. The control unit 260 of the endoscope 200 and the light source and image processing apparatus 310 are connected by a universal cable 290. A connector 292 is provided on an end of the universal cable 290, and the light source and image processing apparatus 310 and the universal cable 290 are connected using the connector 292. The light source and image processing apparatus 310 and the control apparatus 100 are connected, and the endoscope 200 and the control apparatus 100 are connected through the light source and image processing apparatus 310.

The insertion section 210 includes a distal end hard section 212, a bending section 214, and a coiled hose section 216. The distal end hard section 212 is an edge of the distal end of the insertion section 210, and is configured not to be bent. The bending section 214 is a part formed on the proximal end side of the distal end hard section 212, and is configured to be actively bent in accordance with an operation of an operation unit 261 provided in the control unit 260. The coiled hose section 216 is a part formed on the proximal end side of the bending section 214, and is configured to be passively bent by external force.

The distal end hard section 212 includes an imager 220 and an irradiation lens 221. The imager 220 generates an image signal based on a subject image on the distal end side of the insertion section 210, for example. The image signal generated in the imager 220 is transmitted to the light source and image processing apparatus 310 via a non-illustrated signal line for the image signal passing through the insertion section 210 and the universal cable 290. The irradiation lens 221 diffuses and emits light guided from the light source and image processing apparatus 310 through a non-illustrated optical fiber passing through the insertion section 210 and the universal cable 290.

The endoscope system 1 according to the embodiment comprises a self-propelled mechanism 201. That is, to the coiled hose section 216 of the insertion section 210, a rotation unit 230 for transmitting driving power of a motor 252 as a power source built in the control unit 260 is attached. In addition, on the distal end side of the rotation unit 230, a power spiral tube 232 which is a rotational tubular body is attached. The power spiral tube 232 is formed of a soft material such as rubber or a resin, for example, in a tubular shape, and is mounted to be rotatable around a longitudinal axis of the coiled hose section 216. On an outer peripheral surface of the power spiral tube 232, a spiral-shaped fin 234 is provided along the longitudinal axis of the power spiral tube 232. Note that the power spiral tube 232 may be configured to be detachable from the rotation unit 230.

Furthermore, the power spiral tube 232 is connected to the motor 252 as an actuator provided in the control unit 260. The motor 252 is connected to the control apparatus 100 via a non-illustrated signal line for an actuator current signal passing through the control unit 260 and the universal cable 290.

The motor 252 operates by an operation using a foot switch 180. The rotation power of the motor 252 is transmitted to the rotation unit 230. As a result, the fin 234 provided in the power spiral tube 232 rotates around the longitudinal axis.

When the fin 234 rotates in the state of being in contact with a wall part such as an inner paries of a lumen, propulsive force is generated to allow the insertion section 210 to self-propel. For example, in a small intestine or a large intestine, when the fin 234 draws folds present in the inner paries of the small intestine or the large intestine, the propulsive force is applied to the insertion section 210. The insertion section 210 self-propels by the propulsive force. The self-propelling of the insertion section 210 assists an insertion operation and a removal operation of the insertion section 210 by the user. Note that in the following description, a rotating direction of the motor 252 to allow the insertion section 210 self-propel to the distal end side is referred to as a normal rotation direction (insertion direction), and a rotating direction of the motor 252 to allow the insertion section 210 self-propel to the proximal end side is referred to as a reverse rotation direction (removal direction).

The self-propelled mechanism 201 according to the embodiment is configured such that, when torque generated in the motor 252 exceeds a predetermined limit value, the rotation of the motor 252 is temporarily stopped and insertion of the insertion section 210 is temporarily interrupted. Such temporary stop of the rotation of the motor 252 contributes to preventing damages to the inner paries of the lumen and to avoiding a failure of the self-propelled mechanism 201 or the like.

Near the motor 252, an encoder 254 is provided. The encoder 254 generates a pulse signal (rotational speed signal) in accordance with a rotational speed of the motor 252. The rotational speed signal is transmitted to the control apparatus 100 via a non-illustrated rotational speed signal line passing through the universal cable 290. In the self-propelled mechanism 201, the rotation of the motor 252 is controlled with the rotational speed as a feedback value.

The display 320 includes a general display element such as a liquid crystal display. The display 320 displays an endoscope image based on the image signal obtained in the imager 220 for example. The display 320 may display the state of the self-propelled mechanism 201. Information displayed on the display 320 may include error display which reports abnormality of the self-propelled mechanism 201 to the user.

The foot switch 180 includes a forward (F) pedal 182 and a backward (B) pedal 184. The F-pedal 182 is the pedal to be stepped on when the user wants the motor 252 to normally rotate. The B-pedal 184 is the pedal to be stepped on when the user wants the motor 252 to reversely rotate. The F-pedal 182 and the B-pedal 184 are configured such that a stepping amount is detected as an input state, respectively. In addition, the foot switch 180 comprises a diagnosis circuit 186 which diagnoses the state of the foot switch 180. The diagnosis circuit 186 operates with power supplied from the control apparatus 100, and transmits a diagnosis result to the control apparatus 100.

A torque indicator 190 is a display apparatus configured using display elements such as LEDs, and displays a value relating to the torque generated by the motor 252. The torque indicator 190 includes a display area which indicates the magnitude of the torque on the normal rotation side and the magnitude of the torque on the reverse rotation side for example by the number of lights of the respective display elements. In addition, the torque indicator 190 may be configured to perform error display which reports the abnormality of the self-propelled mechanism 201 to the user.

Figure 2:
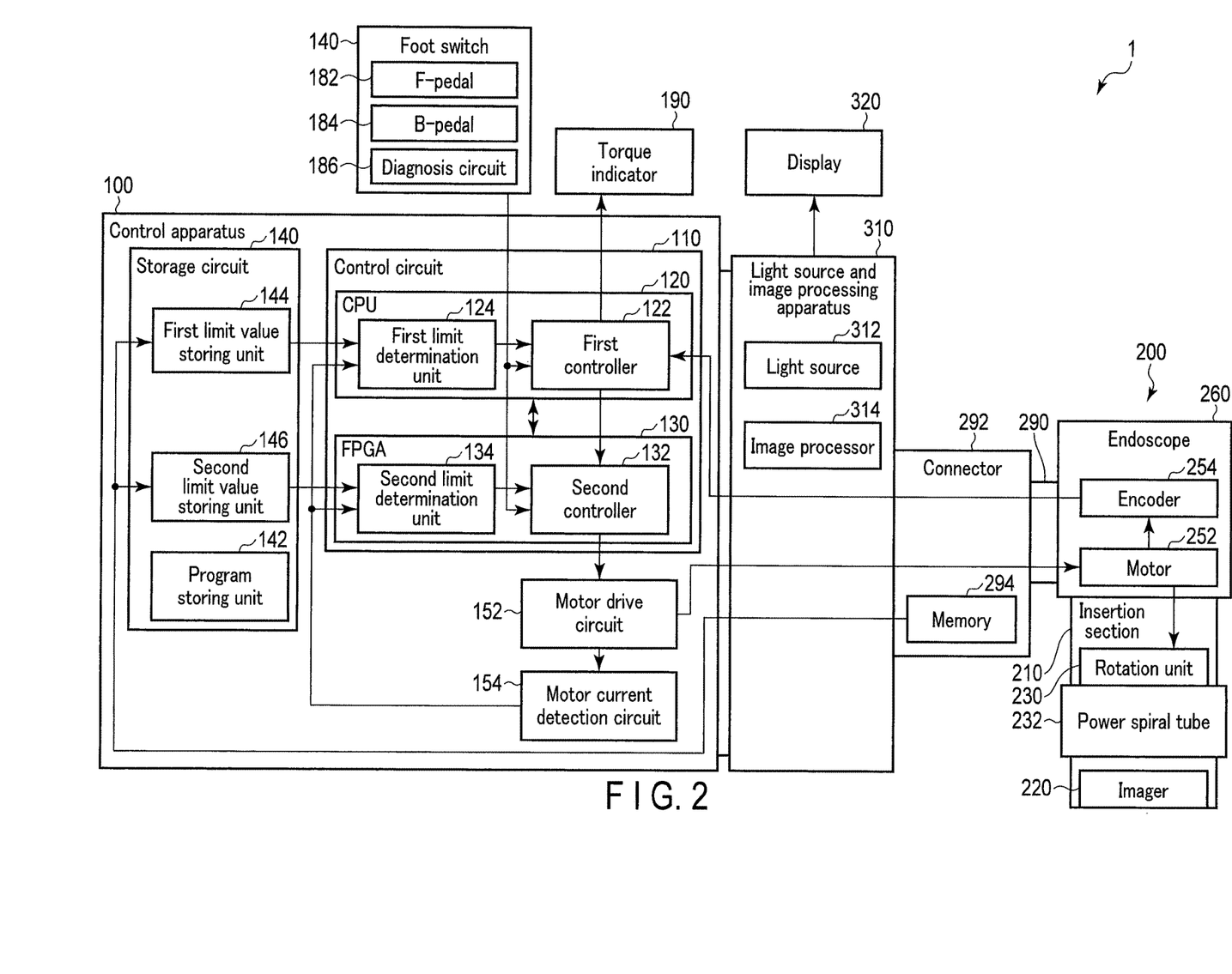
FIG. 2 is a schematic block diagram illustrating the endoscope system configuration example according to an embodiment.

FIG. 2 is a schematic block diagram illustrating a configuration example of the endoscope system 1. As illustrated in FIG. 2, the light source and image processing apparatus 310 includes a light source 312 and an image processor 314. The light source 312 includes a white LED or a xenon lamp or the like for example, and inputs light to a non-illustrated optical fiber inside the universal cable 290. The light is guided to the distal end of the insertion section 210, and is emitted from the irradiation lens 221. The image processor 314 acquires the image signal from the imager 220 via the insertion section 210 and the universal cable 290. The image processor 314 executes image processing to the acquired image signal. In addition, the image processor 314 transmits the processed image signal to the display 320, and makes the display 320 display the endoscope image.

The control apparatus 100 controls the operation of the self-propelled mechanism 201. The control apparatus 100 comprises a control circuit 110, a storage circuit 140, a motor drive circuit 152, and a motor current detection circuit 154.

The control circuit 110 controls the operation of the self-propelled mechanism 201 and display of the torque indicator 190 or the like. The control circuit 110 includes a central processing unit (CPU) 120, and a field programmable gate array (FPGA) 130. The CPU 120 functions as a software controller which performs various kinds of processing based on software. Processing content of the FPGA 130 is set by hardware, and the FPGA 130 functions as a hardware controller which performs various kinds of processing by the hardware. The CPU 120 and the FPGA 130 exchange data. Instead of the FPGA, a circuit programmed by hardware such as an application specific integrated circuit (ASIC) may be used. Note that, here, for the control circuit 110, an example in which the CPU 120 and the FPGA 130 are provided as an integrated circuit is described, but the CPU 120 and the FPGA 130 may be provided as a plurality of integrated circuits.

The motor drive circuit 152 includes a driver amplifier circuit for example. The motor drive circuit 152 outputs a motor current to drive the motor 252, based on a command value received from the control circuit 110. As a result, the motor 252 normally rotates at a rotational speed in accordance with the magnitude of stepping of the F-pedal 182. In addition, the motor 252 reversely rotates at the rotational speed in accordance with the magnitude of stepping of the B-pedal 184.

The motor current detection circuit 154 detects a value relating to a current outputted from the motor drive circuit 152 to the motor 252. The motor current detection circuit 154 transmits a signal relating to the detected output current to the control circuit 110.

The storage circuit 140 is a recording medium in which content is preserved even when a power source is turned off, a flash memory for example. The storage circuit 140 includes a program storing unit 142 in which a program used by the CPU 120 of the control circuit 110 is recorded, for example. In addition, the storage circuit 140 includes a first limit value storing unit 144 which records a first limit value to be described later and a second limit value storing unit 146 which records a second limit value. The storage circuit 140 is not limited to a semiconductor memory, and may be a medium using a magnetism or light or the like. That is, various kinds of recording media may be in charge of the function of the storage circuit 140.

The CPU 120 of the control circuit 110 achieves the function as a first controller 122 and a first limit determination unit 124. The FPGA 130 achieves the function as a second controller 132 and a second limit determination unit 134.

The first controller 122 detects that the F-pedal 182 or the B-pedal 184 is stepped by the user, and the stepping amount. In addition, the first controller 122 fetches the rotational speed signal inputted from the encoder 254 at every predetermined sampling period. The first controller 122 prepares the command value relating to the motor current outputted from the motor drive circuit 152. The command value is calculated as a value by which the motor 252 rotates at the rotational speed in accordance with the stepping amount of the F-pedal 182 or the B-pedal 184, with the rotational speed signal as a feedback signal. That is, the first controller 122 calculates the command value based on a difference between a current motor speed and a target motor speed. A control signal which includes the command value is outputted to the motor drive circuit 152 through the second controller 132 of the FPGA 130.

The first limit determination unit 124 determines whether or not the torque of the motor 252 exceeds the first limit value, and when exceeding the first limit value, stops the rotation of the motor 252. Here, the torque of the motor 252 is indicated based on the motor current supplied to the motor 252. Thus, the first limit value is the value relating to the motor current. The first limit determination unit 124 reads the first limit value from the first limit value storing unit 144 of the storage circuit 140. The first limit determination unit 124 acquires the signal relating to the magnitude of the motor current outputted from the motor drive circuit 152, from the motor current detection circuit 154. The first limit determination unit 124 determines whether or not the motor current exceeds the first limit value. When it is determined that the motor current exceeds the first limit value, the first limit determination unit 124 determines to limit a torque. Here, limiting the torque is to stop the output of the motor current from the motor drive circuit 152 to the motor 252. When it is determined to limit the torque, the first limit determination unit 124 transmits that effect to the first controller 122. At the time, the first controller 122 stops the motor 252. That is, the first controller 122 stops the output of the control signal to the motor drive circuit 152.

The first controller 122 acquires information relating to the magnitude of the motor current detected in the motor current detection circuit 154 through the first limit determination unit 124. The first controller 122 makes the torque indicator 190 display the value relating to the torque generated by the motor 252, based on the magnitude of the motor current.

The second controller 132 of the FPGA 130 transmits the control signal outputted from the first controller 122 to the motor drive circuit 152, and makes the motor drive circuit 152 operate based on the control signal. At the time, the second controller 132 monitors presence/absence of stepping of the F-pedal 182 and the B-pedal 184 of the foot switch 180. When detecting that it is commanded to make the motor 252 rotate from the first controller 122 even though the foot switch is not stepped on, the second controller 132 shuts off the control signal from the second controller 132 to the motor drive circuit 152, and stops the operation of the motor 252.

The second limit determination unit 134 determines whether or not the torque of the motor 252 exceeds a second limit value, and when exceeding the second limit value, stops the rotation of the motor 252. Since the torque of the motor 252 is indicated based on the motor current supplied to the motor 252, the second limit value is also the value relating to the motor current. The second limit determination unit 134 reads the second limit value from the second limit value storing unit 146 of the storage circuit 140. Here, the second limit value may be larger than the first limit value used in the first limit determination unit 124 for example. The second limit determination unit 134 acquires the signal relating to the magnitude of the motor current outputted from the motor drive circuit 152, from the motor current detection circuit 154. The second limit determination unit 134 determines whether or not the motor current exceeds the second limit value. When it is determined that the motor current exceeds the second limit value, the second limit determination unit 134 determines to limit the torque. When it is determined to limit the torque, the second limit determination unit 134 transmits that effect to the second controller 132. At the time, the second controller 132 shuts off the control signal from the second controller 132 to the motor drive circuit 152, and stops the operation of the motor 252.

Note that, in the embodiment, the connector 292 of the endoscope 200 for example is provided with a memory 294. In the memory 294, the values relating to the first limit value and the second limit value are recorded. Since it is sometimes preferable that the limit value is set to be different for each endoscope 200, it is preferable that an appropriate limit value is recorded in the memory 294 for each endoscope 200. It is preferable that the control apparatus 100 reads the limit value recorded in the memory 294 and achieve a torque limit function described above. That is, the control circuit 110 reads the limit value recorded in the memory 294, and stores the first limit value and the second limit value in the first limit value storing unit 144 and the second limit value storing unit 146 of the storage circuit 140 respectively.

[Operation of Endoscope System]

Figure 3:
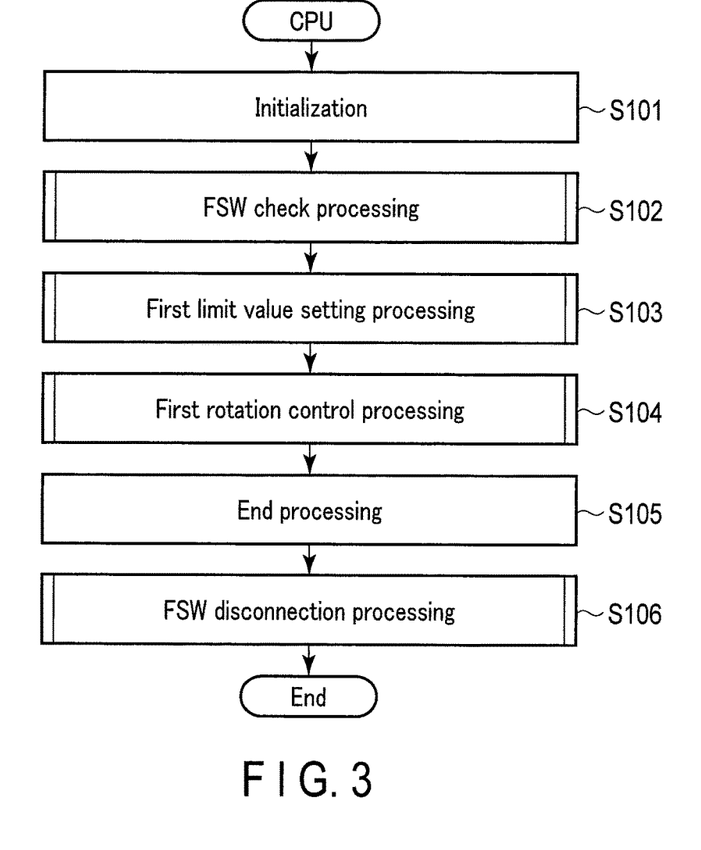
FIG. 3 is a flowchart illustrating a schematic example of main processing performed in a CPU of a control apparatus according to an embodiment.
Figure 4:
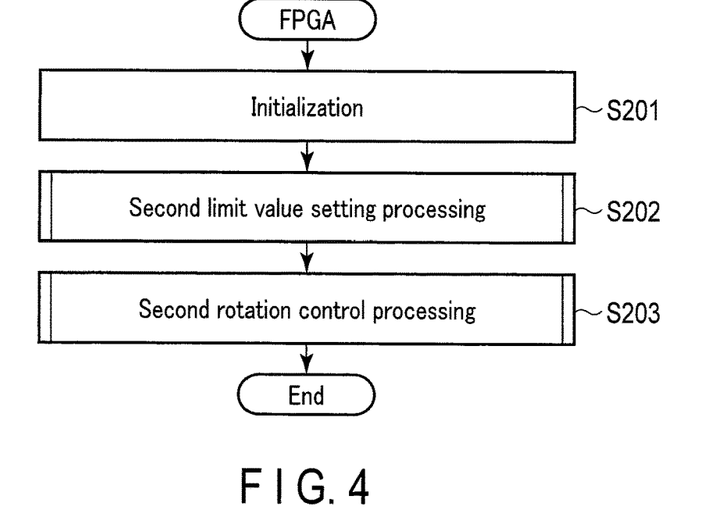
FIG. 4 is a flowchart illustrating a schematic example of main processing performed in an FPGA of the control apparatus according to an embodiment.

The operation of the endoscope system 1 will be described. FIG. 3 illustrates a schematic example of processing performed in the CPU 120 included in the control circuit 110. FIG. 4 illustrates a schematic example of processing performed in the FPGA 130 included in the control circuit 110. The operation of the CPU 120 illustrated in FIG. 3 is performed according to the program stored in the program storing unit 142, when a power source of the endoscope system 1 is turned on. The operation of the FPGA 130 illustrated in FIG. 4 is performed in accordance with the mounted hardware, when the power source of the endoscope system 1 is turned on. In parallel with the operations, in the light source and image processing apparatus 310, processing of making the display 320 display the endoscope image based on the image signal obtained in the imager 220 or the like is performed.

<Main Processing of CPU>

An outline of the processing performed in the CPU 120 will be described with reference to a flowchart illustrated in FIG. 3.

In step S101, the CPU 120 performs various kinds of initializations relating to the control apparatus 100. In step S102, the CPU 120 performs FSW check processing of performing the initialization regarding the foot switch (FSW) 180. In the FSW check processing, whether or not the foot switch 180 is normal is determined. The FSW check processing will be described later in detail.

In step S103, the CPU 120 performs first limit value setting processing. In the first limit value setting processing, the first limit value used in the first limit determination unit 124 is set. The first limit value setting processing will be described later in detail. After the various kinds of setting above, the processing advances to step S104.

In step S104, the CPU 120 performs first rotation control processing. In the first rotation control processing, the CPU 120 prepares the control signal which makes the motor 252 rotate in accordance with input to the foot switch 180. In addition, the CPU 120 determines a limit such that the output torque of the motor 252 does not become equal to or larger than the limit value. In this way, the first rotation control processing is the processing performed when the endoscope system 1 is in use. The first rotation control processing will be described later in detail. When the use of the endoscope system 1 is ended and the power source is turned off, the processing advances to step S105.

In step S105, the CPU 120 performs various kinds of end processing. That is, the end processing of an unneeded program or the like is performed, and power supply to an unneeded part is shut off. In step S106, the CPU 120 performs FSW disconnection processing. In the FSW disconnection processing, the CPU 120 shuts off the power supply to the foot switch 180. Thus, the processing by the CPU 120 is ended.

<Main Processing of FPGA>

The outline of the processing performed in the FPGA 130 will be described with reference to a flowchart illustrated in FIG. 4.

In step S201, the FPGA 130 performs the various kinds of initializations relating to the operation of the FPGA 130. In step S202, the FPGA 130 performs second limit value setting processing. In the second limit value setting processing, the second limit value used in the second limit determination unit 134 is set. The second limit value setting processing will be described later in detail. After the various kinds of setting above, the processing advances to step S203.

In step S203, the FPGA 130 performs second rotation control processing. In the second rotation control processing, the FPGA 130 outputs the control signal prepared in the CPU 120 to the motor drive circuit 152. At the time, the FPGA 130 determines the limit such that the output torque of the motor 252 does not become equal to or larger than the limit value. In this way, the second rotation control processing is the processing performed when the endoscope system 1 is in use. The second rotation control processing will be described later in detail. When the use of the endoscope system 1 is ended and the power source is turned off, the processing of the FPGA 130 is ended.

<FSW Check Processing of CPU>

Figure 5:
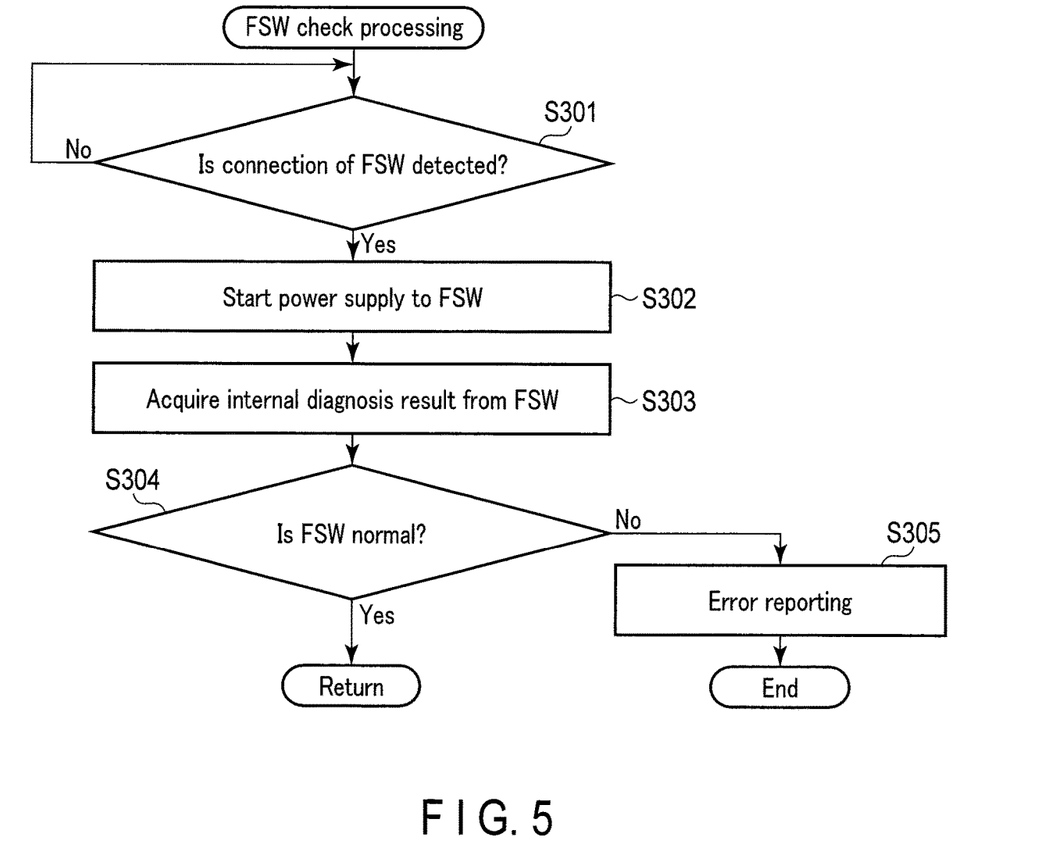
FIG. 5 is a flowchart illustrating a schematic example of FSW check processing performed in the CPU of the control apparatus according to an embodiment.

The FSW check processing performed in step S102 by the CPU 120 will be described with reference to a flowchart illustrated in FIG. 5. The FSW check processing is the processing relating to a self-diagnosis function performed in the foot switch 180. The foot switch 180 itself is not provided with a power source, and executes self-diagnosis using the power supplied from the control apparatus 100. Therefore, in the FSW check processing, timing of the power supply to the foot switch and timing of acquisition of a self-diagnosis result are adjusted.

In step S301, the CPU 120 determines whether or not the foot switch 180 is connected to the control apparatus 100. When the foot switch 180 is not connected, the processing repeats step S301 and stands by. On the other hand, when the foot switch is connected, the processing advances to step S302.

In step S302, the CPU 120 starts the power supply to the foot switch 180 from the control apparatus 100. The diagnosis circuit 186 of the foot switch 180 supplied with the power performs the self-diagnosis inside the foot switch 180 to see whether or not the foot switch 180 is abnormal or the like. The diagnosis circuit 186 transmits a diagnosis result to the control circuit 110 in accordance with a request from the CPU 120.

In step S303, the CPU 120 acquires the result of internal diagnosis from the foot switch 180. At the time, the CPU 120 acquires the result of the internal diagnosis at the timing for which the time after the power supply to the foot switch 180 is started until the result of the self-diagnosis is acquired is taken into consideration.

In step S304, the CPU 120 determines whether or not the foot switch 180 is normal, based on the diagnosis result of the foot switch 180. When the foot switch 180 is normal, the FSW check processing is ended, and the processing returns to the main processing of the CPU 120, and advances to the first limit value setting processing in step S103.

When it is determined that the foot switch 180 is not normal in step S304, the processing advances to step S305. In step S305, the CPU 120 performs error reporting processing. For example, the CPU 120 makes the display 320 or the torque indicator 190 display that the foot switch 180 is abnormal. Thereafter, the CPU 120 ends the series of processing. The control apparatus 100 may report an error to the user by sound.

By the FSW check processing, the foot switch 180 can accurately perform the self-diagnosis, and the CPU 120 can accurately acquire the result. If the connection of the foot switch 180 is not confirmed as in the FSW check processing, it is possible that the CPU 120 tries to acquire the self-diagnosis result from the foot switch 180 which is yet to be connected to the control apparatus 100 and in which the self-diagnosis is not performed, for example. In such a case, it is possible that the CPU 120 determines that the foot switch 180 is abnormal and ends the processing even though the foot switch 180 is not abnormal. According to the FSW check processing, the CPU 120 can prevent such a malfunction.

<First Limit Value Setting Processing of CPU>

Figure 6:
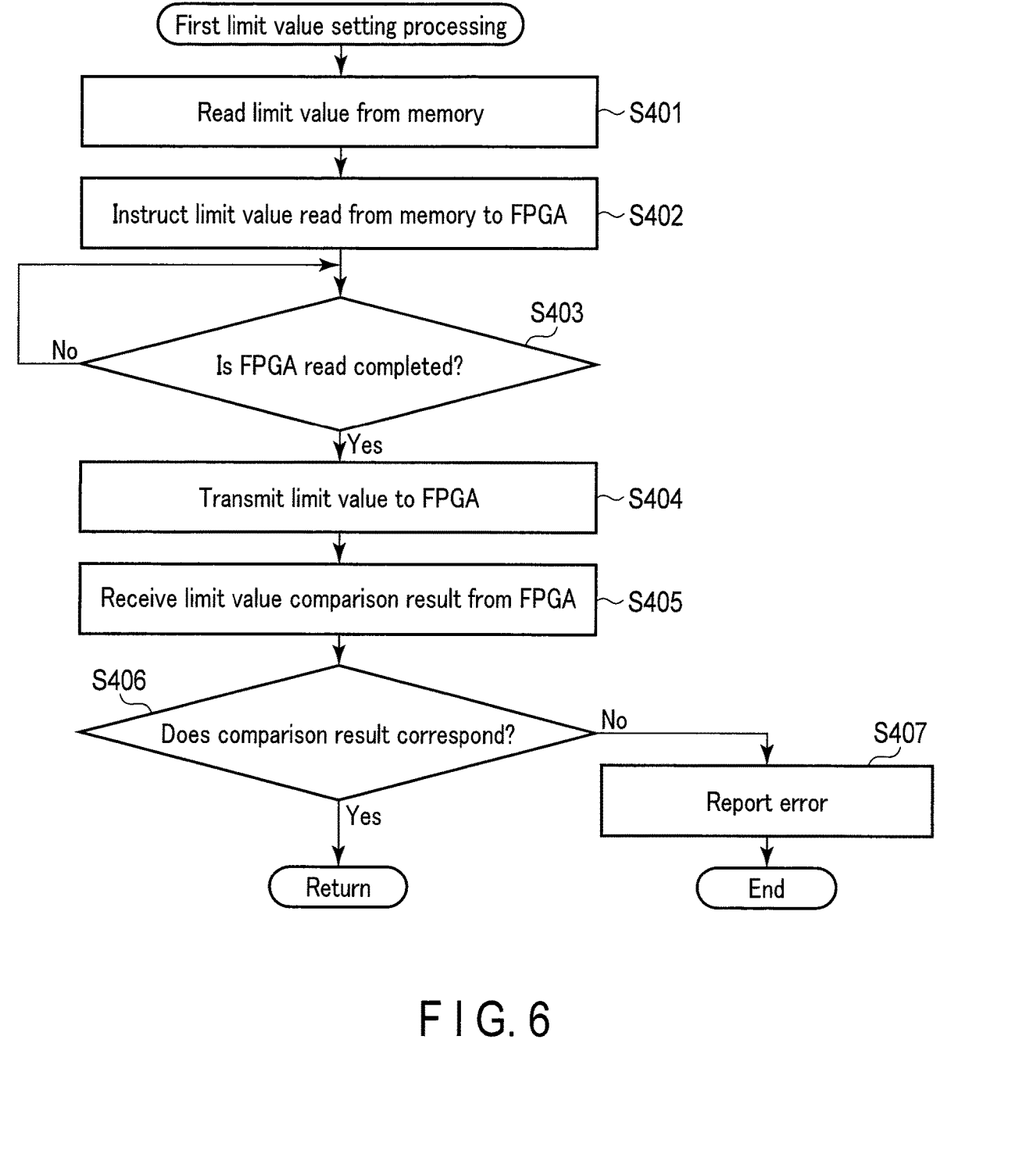
FIG. 6 is a flowchart illustrating a schematic example of first limit value setting processing performed in the CPU of the control apparatus according to an embodiment.

The first limit value setting processing performed in step S103 by the CPU 120 will be described with reference to a flowchart illustrated in FIG. 6.

In step S401, the CPU 120 reads the limit value used in the CPU 120 from the memory 294 provided in the connector 292 of the endoscope 200, and stores the limit value in the first limit value storing unit 144 of the storage circuit 140. In step S402, the CPU 120 outputs an instruction to read the limit value from the memory 294, to the FPGA 130. The FPGA 130 which receives the instruction reads the limit value used in the FPGA 130 from the memory 294.

In step S403, the CPU 120 determines whether or not information that read of the limit value is completed is received from the FPGA 130. The CPU 120 stands by until the information that the read of the limit value is completed is received from the FPGA 130. When the CPU 120 receives the information that the read of the limit value is completed from the FPGA 130, the processing advances to step S404.

In step S404, the CPU 120 transmits the limit value read by the CPU 120 to the FPGA 130. The FPGA 130 which receives the limit value transmitted from the CPU 120 compares the received limit value with the read limit value and transmits a comparison result to the CPU 120, as described later.

In step S405, the CPU 120 receives the comparison result of the limit values from the FPGA 130. In step S406, the CPU 120 determines whether or not the limit value read by the CPU 120 and the limit value read by the FPGA 130 correspond such that a difference between the limit values is in a predetermined range or the like, in the comparison result. When it is determined that both limit values correspond, the first limit value setting processing is ended, and the processing returns to the main processing of the CPU 120 and advances to the first rotation control processing in step S104. On the other hand, when it is determined that both limit values do not correspond, the processing advances to step S407.

In step S407, the CPU 120 reports the error. That is, it is notified to the user that error occurrence is detected in the control apparatus 100. Various methods such as the display at the torque indicator 190 or the display 320 and sound output may be used to report the error. Thereafter, the CPU 120 ends the series of processing.

<Second Limit Value Setting Processing of FPGA>

Figure 7:
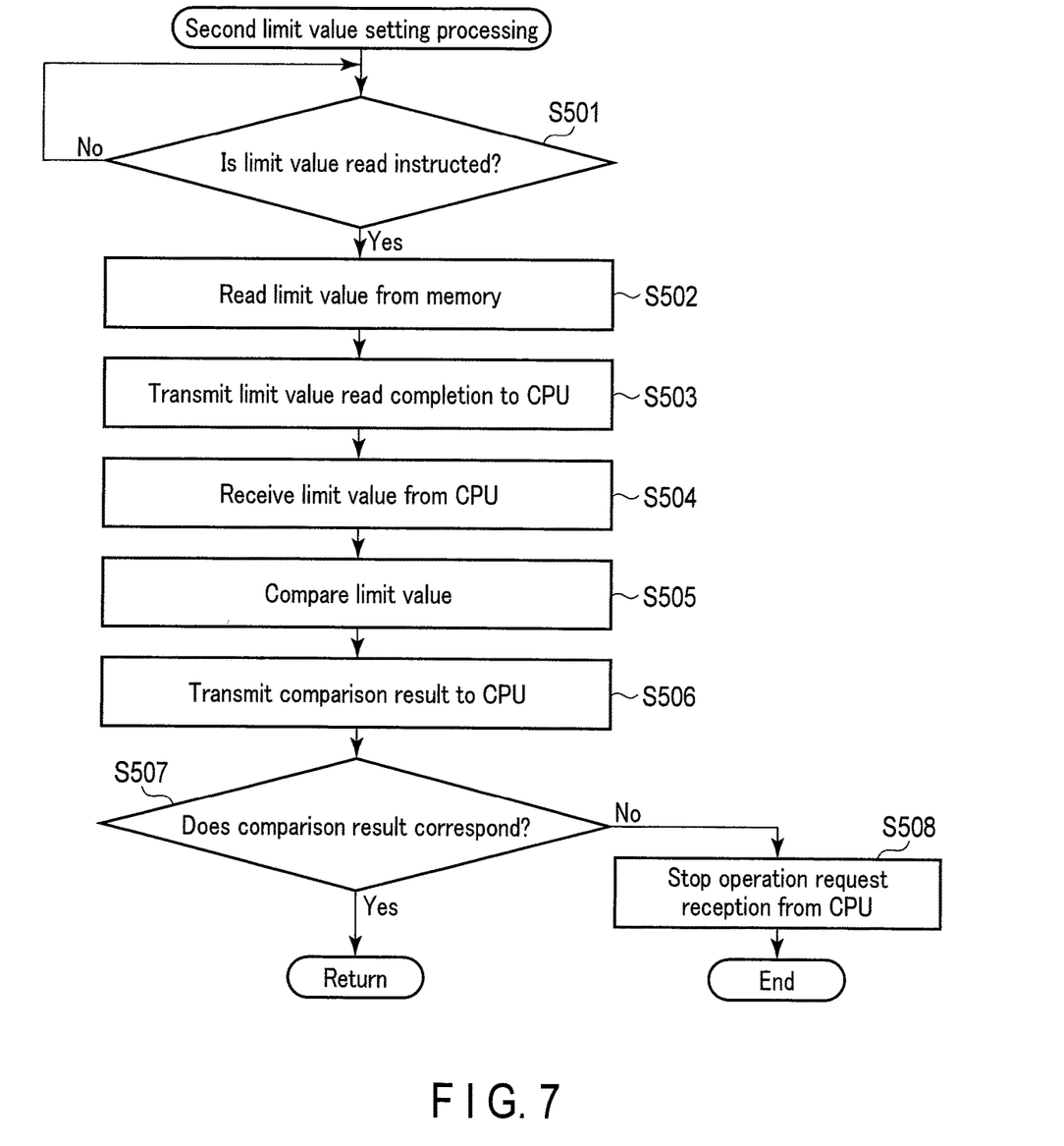
FIG. 7 is a flowchart illustrating a schematic example of second limit value setting processing performed in the FPGA of the control apparatus according to an embodiment.

The second limit value setting processing performed in step S202 by the FPGA 130 while the first limit value setting processing is performed will be described with reference to a flowchart illustrated in FIG. 7.

In step S501, the FPGA 130 determines whether or not the instruction to read the limit value is received. Here, the instruction to read the limit value is the instruction outputted in step S402 of the first limit value setting processing by the CPU 120. The FPGA 130 stands by until it is instructed to read the limit value. When the instruction to read the limit value is received, the processing advances to step S502.

In step S502, the FPGA 130 reads the limit value from the memory 294 of the endoscope 200. The FPGA 130 stores the read limit value in the second limit value storing unit 146. In step S503, the FPGA 130 transmits the fact that the read of the limit value is completed to the CPU 120. In accordance with the signal, the CPU 120 transmits the limit value read in the CPU in step S404 to the FPGA 130. In step S504, the FPGA 130 receives the limit value transmitted from the CPU 120.

In step S505, the FPGA 130 compares the limit value read by the FPGA 130 and the limit value read by the CPU 120 and received from the CPU 120, and determines whether or not the limit values correspond. In step S506, the FPGA 130 transmits the comparison result of the limit values to the CPU 120. The comparison result is received in the CPU 120 in step S405.

In step S507, the FPGA 130 determines whether or not the comparison result of the limit value read by the FPGA 130 and the limit value read by the CPU 120 corresponds. When the comparison result corresponds, the second limit value setting processing is ended, and the processing returns to the main processing of the FPGA 130 and advances to the second rotation control processing in step S203.

When it is determined that the comparison result does not correspond in step S507, the processing advances to step S508. In step S508, the FPGA 130 stops reception of the request to operate the motor 252 from the CPU 120. When the comparison result does not correspond, the CPU 120 reports the error and ends the series of processing as described above. Thus, when the control circuit 110 normally operates, the control signal which makes the motor 252 operate is not transmitted from the CPU 120 to the FPGA 130. However, the control signal to operate the motor 252 may be transmitted from the CPU 120 to the FPGA 130 due to operation abnormality of the CPU 120 for example. In the embodiment, even in such a case, the FPGA 130 stops the reception of the request to operate the motor 252 from the CPU 120. As a result, when the comparison result does not correspond, the control signal for making the motor 252 rotate is not outputted from the FPGA 130 to the motor drive circuit 152. After the processing of step S508, the FPGA 130 ends the series of processing.

As described above, the limit values recorded in the memory 294 of the endoscope 200 are stored in the first limit value storing unit 144 and the second limit value storing unit 146.

Whether or not the torque exceeds the limit value is determined in both of the CPU 120 and the FPGA 130. Here, the control apparatus 100 is configured such that the CPU 120 determines that the torque exceeds the limit value before the FPGA 130. That is, a condition to stop the motor 252 by the software by the CPU 120 is the condition satisfied before a condition to stop the motor 252 by the hardware by the FPGA 130. Thus, for example, the first limit value stored in the first limit value storing unit 144 and used in the CPU 120 may be a value smaller than the second limit value stored in the second limit value storing unit 146 and used in the FPGA 130. Also, the first limit value stored in the first limit value storing unit 144 and used in the CPU 120 and the second limit value stored in the second limit value storing unit 146 and used in the FPGA 130 may be identical and the determination made in the CPU 120 and the determination made in the FPGA 130 may be appropriately adjusted. Comparison performed in step S505 is appropriately adjusted in accordance with the circumstances.

<First Rotation Control Processing of CPU>

Figure 8:
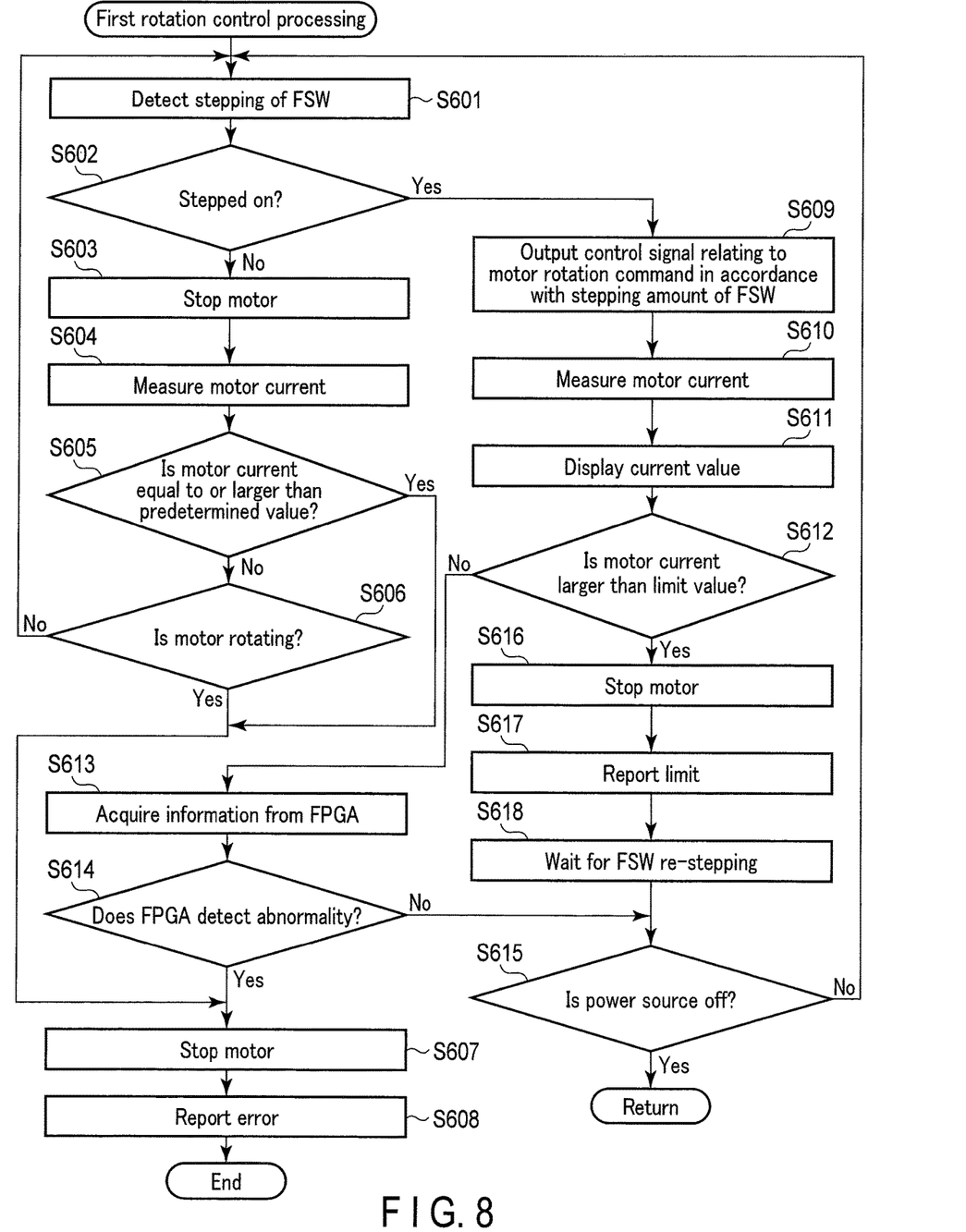
FIG. 8 is a flowchart illustrating a schematic example of first rotation control processing performed in the CPU of the control apparatus according to an embodiment.

The first rotation control processing performed in step S104 by the CPU 120 will be described with reference to a flowchart illustrated in FIG. 8. The first rotation control processing is the operation when an essential function provided in the self-propelled mechanism 201 is used.

In step S601, the CPU 120 acquires the information relating to stepping of the foot switch 180 stepped on by the user. In step S602, the CPU 120 determines whether or not the foot switch 180 is stepped on, based on the acquired information. When it is determined that the foot switch 180 is not stepped on, the processing advances to step S603.

In step S603, the CPU 120 stops the rotation of the motor 252. For example, the CPU 120 stops the output of the control signal outputted to the motor drive circuit 152 through the FPGA 130. In step S604, the CPU 120 acquires the value of the motor current outputted from the motor drive circuit 152 to the motor 252, from the motor current detection circuit 154.

In step S605, the CPU 120 determines whether or not the motor current is equal to or larger than a predetermined value. The predetermined value used here may be the first limit value, or may be other values. When the motor current is smaller than the predetermined value, the processing advances to step S606. In step S606, the CPU 120 acquires the information relating to the rotation of the motor 252 measured using the encoder 254, and determines whether or not the motor is rotating. When the motor is not rotating, the processing returns to step S601. When the foot switch 180 is not stepped on, the motor current is not outputted and the motor 252 does not rotate. When the foot switch 180 is not stepped on, since the state where the motor current is smaller than the predetermined value and the motor is not rotating is normal, the above-described processing is repeated when the state is normal.

When it is determined that the motor current is equal to or larger than the predetermined value in step S605, the processing advances to step S607. In addition, when it is determined that the motor is rotating in step S606, the processing advances to step S607. In step S607, the CPU 120 outputs the signal to stop the motor 252. For example, the FPGA 130 which receives the stop signal shuts off the output of the control signal to the motor drive circuit 152. In step S608, the CPU 120 performs error reporting to report to the user that the operation of the system including the self-propelled mechanism 201 is abnormal. Thereafter, the first rotation control processing is ended. That is, the operation of the self-propelled mechanism 201 is stopped.

When it is determined that the foot switch 180 is stepped on in the determination in step S602, the processing advances to step S609. In step S609, the CPU 120 outputs the control signal relating to the command for making the motor 252 rotate in accordance with the stepping amount of the foot switch 180. That is, the CPU 120 turns the control signal outputted to the motor drive circuit 152 through the FPGA 130 to the signal according to the stepping amount of the foot switch 180. The motor drive circuit 152 which receives the signal outputs the power according to the stepping amount of the foot switch 180 to the motor 252.

In step S610, the CPU 120 acquires the value relating to the motor current outputted from the motor drive circuit 152 to the motor 252, from the motor current detection circuit 154. In step S611, the CPU 120 makes the torque indicator 190 display the acquired current value as the torque generated in the motor 252.

In step S612, the CPU 120 determines whether or not the motor current acquired in step S610 is larger than the first limit value stored in the first limit value storing unit 144. When it is determined that the motor current is not larger than the first limit value, the processing advances to step S613.

In step S613, the CPU 120 acquires the information indicating whether or not the system including the self-propelled mechanism 201 is normally operating from the FPGA 130. In step S614, the CPU 120 determines whether or not the FPGA 130 detects the abnormality, based on the acquired information. When it is determined that the abnormality is detected, the processing advances to step S607. That is, the signal to stop the motor 252 is outputted, the error reporting is performed, and the first rotation control processing is ended.

When it is determined that the FPGA 130 does not detect the abnormality in step S614, the processing advances to step S615. In step S615, the CPU 120 determines whether or not the power source relating to the self-propelled mechanism 201 is turned off. When the power source is not turned off, the processing returns to step S601. On the other hand, when the power source is turned off, the first rotation control processing is ended, and the processing returns to the main processing and advances to step S105.

When it is determined that the motor current is larger than the first limit value in step S612, the processing advances to step S616. In step S616, the CPU 120 outputs the signal to stop the motor 252. In this way, when the torque generated by the motor 252 exceeds the first limit value, the rotation of the motor 252 is temporarily stopped. In step S617, the CPU 120 reports to the user that the motor current exceeds the first limit value, that is, the torque generated by the motor 252 exceeds the limit value. For example, the CPU 120 makes the torque indicator 190 display that the torque exceeds the limit value. Thereafter, in step S618, the CPU 120 waits for re-stepping of the foot switch 180. In other words, release of the stepping of the stepped foot switch 180 is waited for. When the stepping of the foot switch 180 is released, the processing advances to step S615. That is, the operation relating to the rotation of the motor 252 in accordance with the stepping of the foot switch 180 is repeated until the power source is turned off, or until the abnormality is detected. The user operates the stepping of the foot switch 180 and performs an insertion operation of the insertion section 210 of the endoscope 200. Since the torque higher than needed is not generated because of the torque limit function of the CPU 120, the user can perform the operation at ease.

<Second Rotation Control Processing of FPGA>

Figure 9:
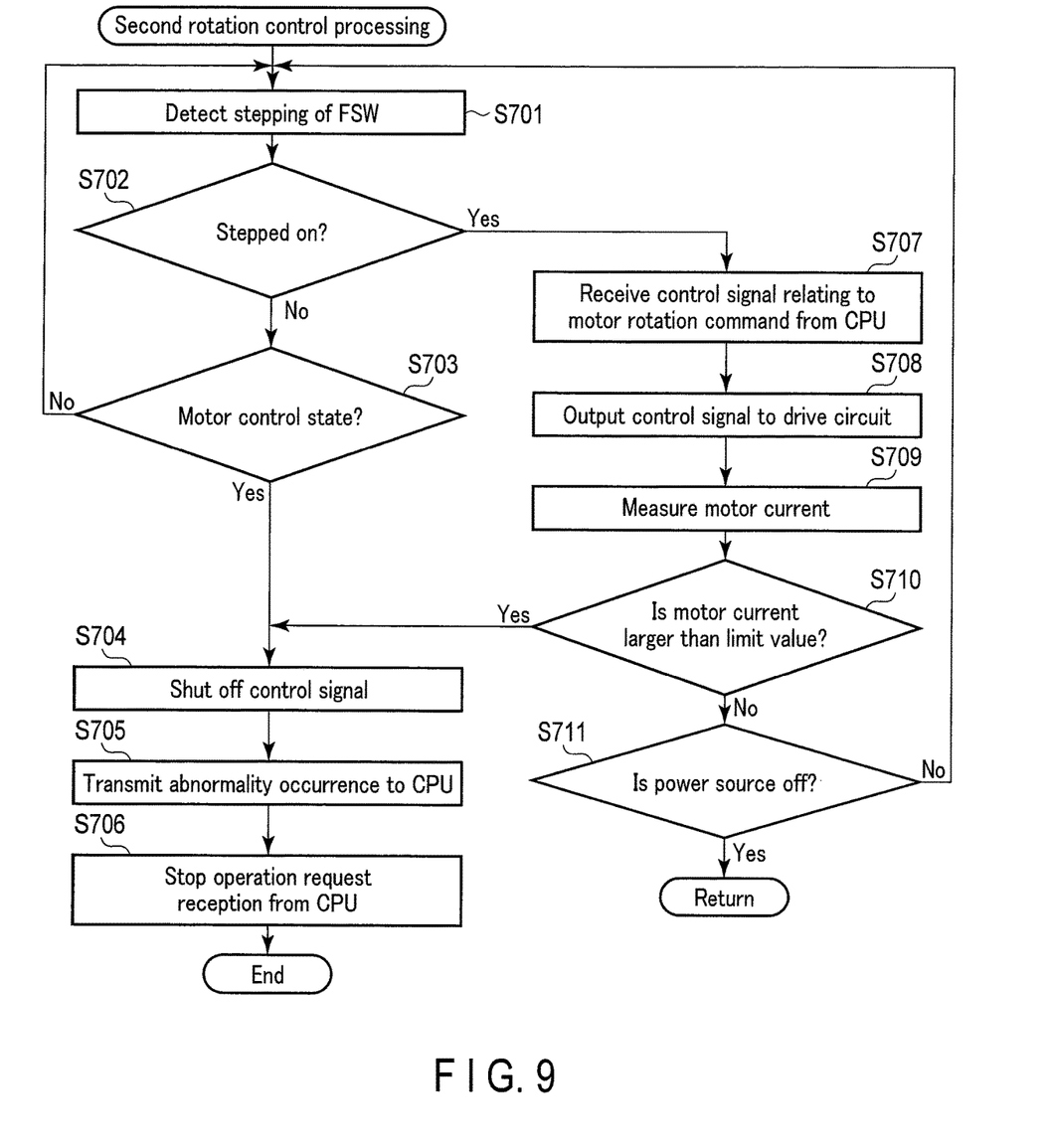
FIG. 9 is a flowchart illustrating a schematic example of second rotation control processing performed in the FPGA of the control apparatus according to an embodiment.

The second rotation control processing performed in the FPGA 130 while the first rotation control processing is performed will be described with reference to a flowchart illustrated in FIG. 9.

In step S701, the FPGA 130 acquires the information relating to the stepping of the foot switch 180. In step S702, the FPGA 130 determines whether or not the foot switch 180 is stepped on, based on the acquired information. When it is determined that the foot switch 180 is not stepped on, the processing advances to step S703.

In step S703, the FPGA 130 monitors the control signal outputted from the CPU 120 to the motor drive circuit 152, and determines whether or not it is a motor control state to make the motor 252 rotate. When it is determined that it is not the motor control state, since it is a normal state, the processing returns to step S701.

When it is determined that it is the motor control state in step S703, the processing advances to step S704. The processing advances to step S704 when it is the motor control state to make the motor 252 rotate even though the foot switch 180 is not stepped on, and when the abnormality occurs. In step S704, the FPGA 130 shuts off the control signal outputted to the motor drive circuit 152. In step S705, the FPGA 130 transmits the occurrence of the abnormality to the CPU 120. Further in step S706, the FPGA 130 stops the reception of the request to operate the motor 252 from the CPU 120. That is, the output of the control signal to the motor drive circuit 152 for making the motor 252 rotate is stopped thereafter. Then, the second rotation control processing is ended.

When it is determined that the foot switch 180 is stepped on in step S702, the processing advances to step S707. In step S707, the FPGA 130 receives the control signal relating to the command to make the motor 252 rotate outputted from the CPU 120. In step S708, the FPGA 130 outputs the received control signal for making the motor 252 rotate to the motor drive circuit 152.

In step S709, the FPGA 130 acquires the value of the motor current outputted from the motor drive circuit 152 to the motor 252, from the motor current detection circuit 154. In step S710, the FPGA 130 determines whether or not the motor current is larger than the second limit value. When the motor current is larger than the second limit value, the processing advances to step S704. When the system is normal, it should be determined by the CPU 120 that the torque exceeds the first limit value first and the motor should be stopped. The processing advances to step S704 when the motor is not stopped and it is determined by the FPGA 130 that the torque exceeds the second limit value nonetheless. In other words, it is when the abnormality occurs somewhere in the system. Then, the FPGA 130 shuts off the control signal to the motor drive circuit 152 in step S704, transmits the abnormality occurrence to the CPU 120 in step S705, stops the reception of the operation request from the CPU 120 in step S706, and ends the second rotation control processing.

When it is determined that the motor current is not larger than the second limit value in step S710, the processing advances to step S711. In step S711, the FPGA 130 determines whether or not the power source of the control apparatus 100 is turned off. When the power source is not turned off, the processing returns to step S701. On the other hand, when the power source is turned off, the second rotation control processing is ended. In this way, the FPGA 130 monitors the operation of the self-propelled mechanism by the system different from the CPU 120, and stops the operation when the abnormality is detected.

<FSW Disconnection Processing of CPU>

Figure 10:
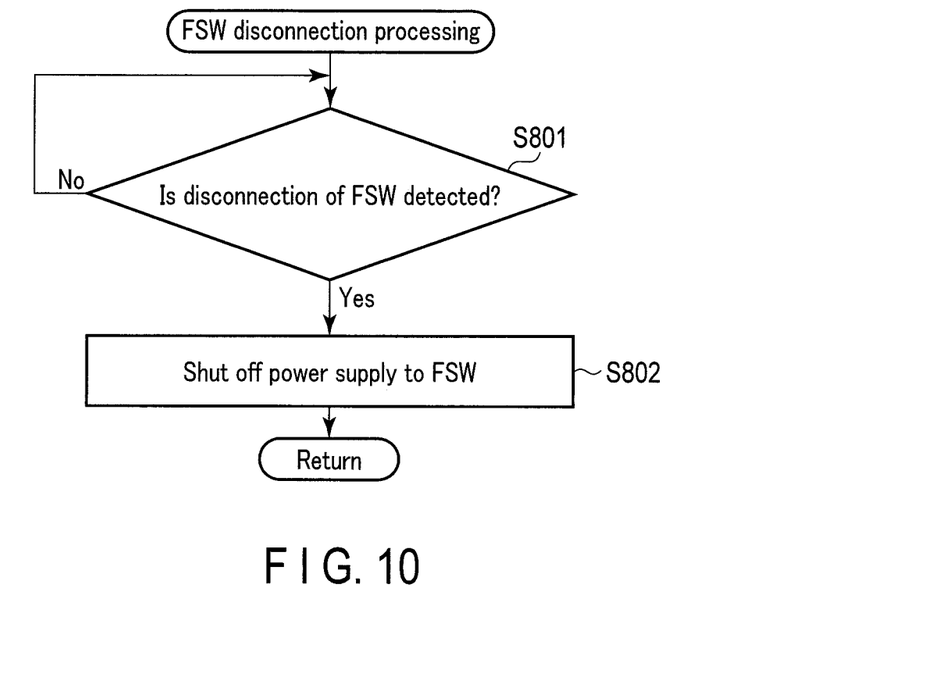
FIG. 10 is a flowchart illustrating a schematic example of FSW disconnection processing performed in the CPU of the control apparatus according to an embodiment.

When the first rotation control processing in step S104 is ended, the CPU 120 performs end processing in step S105, and performs the FSW disconnection processing in step S106. The FSW disconnection processing will be described with reference to a flowchart illustrated in FIG. 10. In step S801, the CPU 120 determines whether or not communication between the foot switch 180 and the control apparatus 100 is disconnected. The processing stands by until the disconnection of the foot switch 180 is detected; When the disconnection of the foot switch 180 is detected, the processing advances to step S802. In step S802, the CPU 120 shuts off the power supply to the foot switch 180. In this way, the control apparatus according to the present embodiment shuts off the power supply to the foot switch 180 when the connection of the foot switch 180 is disconnected.

According to the control apparatus 100 according to the embodiment, even when the torque limit does not appropriately function in the CPU 120, the torque limit can be surely operated in the FPGA 130. In the CPU 120, it is possible that the software performs an abnormal operation. Since the FPGA 130 performs the processing by the hardware independently without being affected by the software, in the control apparatus 100 according to the embodiment, certainty of the operation relating to the torque limit is high compared to the case where only the CPU 120 is in charge of the torque limit function.

Further, in the embodiment, the FPGA 130 monitors a relation between the stepping amount of the foot switch 180 and the control signal outputted by the CPU 120, and when inconsistency is detected for the relation, stops the power supply to the motor 252. By such a function of the FPGA 130, the motor 252 is prevented from rotating due to a failure of the operation of the CPU 120 even though the user does not step on the foot switch 180 for example.

In addition, in the embodiment, the motor current and the rotation of the motor 252 are monitored even when the foot switch 180 is not stepped on. In the case where the motor current flows or the motor 252 rotates even though the foot switch 180 is not stepped on, the FPGA 130 stops the power supply to the motor 252. By such a function of the FPGA 130, the motor 252 is prevented from rotating due to the failure of the operation of the CPU 120 even though the user does not step on the foot switch 180 for example.

[Modification]

The configuration of the self-propelled mechanism 201 illustrated in the embodiment is an example. The self-propelled mechanism may be any configuration. For example, the self-propelled mechanism may be configured such that a belt which rotates in a longitudinal direction of the insertion section 210 is provided on an outer periphery of the insertion section 210.

In the embodiment, the case where the torque limit function is borne by the two systems of the CPU 120 and the FPGA 130 has been described as an example, but it is not limited thereto. For example, the torque limit function may be borne by respective CPUs of the two systems.

The processing described in the above-described embodiment may be partially omitted or replaced, or other processing may be added. For example, the FSW check processing in step S102 or the FSW disconnection processing in step S106 can be omitted. When the limit value is set in the storage circuit 140 beforehand, the first limit value setting processing in step S103 and the second limit value setting processing in step S202 can be omitted. In addition, an order of the processing illustrated in the embodiment may be appropriately changed. Furthermore, whether each processing is performed in the CPU 120 or in the FPGA 130 may be appropriately changed. However, it is preferable to consider that the certainty may be high for the processing of the FPGA 130 independent of the software.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A control apparatus which controls an operation of a self-propelled mechanism of an endoscope including the self-propelled mechanism having a rotatable spiral fin configured to move an insertion section forward or backward with a motor as a power source, the control apparatus comprising:
   a drive circuit configured to output a motor current for driving the motor;
   a motor current detection circuit configured to acquire a detection value relating to a magnitude of the motor current;
   a storage circuit configured to store first and second limit values relating to the detection value; and
   first and second processors configured to control the motor, wherein:
      the first processor is configured to acquire the detection value from the motor current detection circuit, compare the detection value with the first limit value, and stop the motor when the detection value is determined to exceed the first limit value; and
      the second processor is configured to acquire the detection value from the motor current detection circuit, compare the detection value with the second limit value, and stop the motor when the detection value is determined to exceed the second limit value.

2. The control apparatus according to claim 1, wherein the first processor is operated by software, and the second processor is operated by hardware.

3. The control apparatus according to claim 1, wherein the second processor compares the detection value with the second limit value after the first processor compares the detection value with the first limit value.

4. The control apparatus according to claim 1, wherein the second processor stops the motor when the detection value is determined to exceed the second limit value, regardless of the determination by the first processor.

5. The control apparatus according to claim 1,
   wherein the endoscope includes a switch to which an instruction on whether or not to drive the motor by a user is inputted,
   the first processor acquires an input state to the switch, and controls the motor according to the input state, and
   the second processor monitors the input state to the switch, and stops the motor when the first processor controls the motor even though an instruction to drive the motor is not inputted to the switch.

6. The control apparatus according to claim 1,
   wherein the endoscope comprises a memory configured to record the first and second limit values as characteristics of the endoscope, and
   the first processor reads the first limit value recorded in the memory, and stores the first limit value in the storage circuit.

7. The control apparatus according to claim 1,
   wherein the first processor generates a control signal for controlling the motor, and
   the control signal is outputted from the first processor to the drive circuit through the second processor.

8. The control apparatus according to claim 1, wherein the first limit value and the second limit value are identical.

9. The control apparatus according to claim 1, wherein the first limit value is smaller than the second limit value.

10. A self-propelled type endoscope system comprising:
    the control apparatus according to claim 1; and
    the endoscope including the self-propelled mechanism.

11. The self-propelled type endoscope system according to claim 10, wherein the second processor compares the detection value with the second limit value after the first processor compares the detection value with the first limit value.

12. The self-propelled type endoscope system according to claim 10, wherein the second processor stops the motor when the detection value is determined to exceed the second limit value, regardless of the determination by the first processor.

13. The self-propelled type endoscope system according to claim 10,
    wherein the endoscope includes a switch to which an instruction on whether or not to drive the motor by a user is inputted,
    the first processor acquires an input state to the switch, and controls the motor according to the input state, and
    the second processor monitors the input state to the switch, and stops the motor when the first processor controls the motor even though an instruction to drive the motor is not inputted to the switch.

14. The self-propelled type endoscope system according to claim 10,
    wherein the endoscope comprises a memory configured to record the first and second limit values as characteristics of the endoscope, and
    the first processor reads the first limit value recorded in the memory, and stores the first limit value in the storage circuit.

15. The self-propelled type endoscope system according to claim 10,
    wherein the first processor generates a control signal for controlling the motor, and
    the control signal is outputted from the first processor to the drive circuit through the second processor.

16. A control method which controls an operation of a self-propelled mechanism of an endoscope including the self-propelled mechanism having a rotatable spiral fin configured to move an insertion section forward or backward with a motor as a power source, the control method comprising:
    detecting, by first and second processors which control the motor, a motor current which drives the motor as a detection value;
    comparing, by the first processor, the detection value with a first limit value, and stopping the motor when the detection value is determined to exceed the first limit value and,
    comparing, by the second processor, the detection value with a second limit value, and stopping the motor when the detection value is determined to exceed the second limit value.

* * * * *